United States Patent [19]

Cuscurida et al.

[11] Patent Number: 5,068,444

[45] Date of Patent: Nov. 26, 1991

[54] TETRAMINES BY AMINATION OF DIALDEHYDE GLYCOL ADDUCTS

[75] Inventors: Michael Cuscurida; David R. McCoy, both of Austin; Jiang-Jen Lin, Houston, all of Tex.

[73] Assignee: Texaco Chemical Company, White Plains, N.Y.

[21] Appl. No.: 429,671

[22] Filed: Oct. 31, 1989

[51] Int. Cl.$^5$ .................. C07C 215/08; C07C 217/08
[52] U.S. Cl. .................................................. 564/505
[58] Field of Search ............. 564/505, 471, 473, 474, 564/475, 477, 478, 479, 480, 504, 601, 602

[56] References Cited

U.S. PATENT DOCUMENTS

| | | | |
|---|---|---|---|
| 2,923,696 | 2/1960 | Harwell et al. | 260/47 |
| 3,347,926 | 10/1967 | Zech | 260/585 |
| 3,373,204 | 3/1968 | Hales et al. | 260/570.7 |
| 3,390,184 | 6/1968 | Moss et al. | 260/585 |
| 3,654,370 | 4/1972 | Yeakey | 260/584 B |
| 4,130,590 | 12/1978 | Hobbs et al. | 260/585 D |
| 4,364,777 | 12/1982 | Grünert et al. | 134/29 |
| 4,383,100 | 5/1983 | Pechhold | 528/76 |
| 4,409,399 | 10/1983 | Swift et al. | 564/473 |
| 4,691,000 | 9/1987 | Collart et al. | 528/244 |
| 4,745,208 | 5/1988 | Adolph et al. | 558/483 |
| 4,992,595 | 2/1991 | Kleber et al. | 568/601 |

*Primary Examiner*—John Kight, III
*Assistant Examiner*—Shelley Wright
*Attorney, Agent, or Firm*—Jack H. Park; Kenneth R. Priem; David L. Mossman

[57] ABSTRACT

A process in which a dialdehyde is reacted with a polyoxyalkylene glycol to form a dialdehyde glycol condensate which is alkoxylated with propylene oxide, butylene oxide or mixtures thereof and the resulting product is then catalytically aminated to provide, for example, a tetramine is disclosed. These compounds are useful as curing agents for epoxy resins and for reaction with isocyanates to prepare polyurea elastomers and to manufacture articles, such as automotive body panels by reaction injection molding.

10 Claims, No Drawings

TETRAMINES BY AMINATION OF DIALDEHYDE GLYCOL ADDUCTS

CROSS REFERENCE TO RELATED APPLICATIONS

This application is related to U.S. Patent Application for Tetramines by Amination of Polyoxyalkylene Glycols by Jiang-Jen Lin and Michael Cuscurida, attorney's docket number for which is D#80,853 filed of even date and to U.S. Patent Application for Preparation of Aminotetramines by Michael Cuscurida, Wei-Yang Su and George P. Speranza, attorney's docket number for which is D#80,861, filed of even date.

BACKGROUND OF THE INVENTION

1. Field of the Invention

This invention relates to tetramines prepared by amination of alkoxylated dialdehyde glycol adducts. The compounds of this invention are useful as curing agents for epoxy resins and in preparing polyurea and polyurethane products and in making RIM elastomers.

2. Prior Art

The amination of long alkoxylated alkyl chains terminated by hydroxyl groups is well known in the art.

U.S. Pat. No. 3,654,370 to E. L. Yeakey teaches the amination of polyoxyalkylene polyols to form the corresponding amines by means of ammonia and hydrogen over a catalyst prepared by the reduction of a mixture of the oxides of nickel, copper and chromium. The amination is carried out at a temperature of 150° to 275° C. and 500 to 5000 psig.

U.S. Pat. No. 4,409,399 to H. E. Swift et al., teaches a catalyst for aminating aliphatic alcohols and aldehydes. The unsupported catalyst comprises (1) copper oxide or copper hydroxide and (2) nickel oxide or nickel hydroxide, and optionally (3) an oxide or hydroxide of a Group IIA metal; e.g., magnesium or barium. The reaction is carried out at a temperature of 150° to 250° C. and 1 to 100 atm with continuous water removal.

U.S. Pat. No. 3,390,184 to P. H. Moss et al., teaches a process for converting a secondary alcohol to a high-molecular weight primary amine by means of a hydrogenation-dehydrogenation catalyst comprising at least one member selected from the group consisting of the metals and oxides of nickel and cobalt, together with copper and a metal oxide selected from the group consisting of chromium oxide, molybdenum oxide, manganese oxide and thorium oxide. The reaction is carried out at a temperature of 225° to 260° C. and pressure of 2000 to 4000 psig, with ammonia as the aminating agent.

U.S. Pat. No. 3,373,204 to R. A. Hales et al., teaches a catalytic process for producing secondary amines from derivatives of phenols, alcohols and amines containing 5 to 40 moles of ethylene oxide and propylene oxide. The catalyst is Raney nickel and ammonia or primary alkylamines as the aminating agent. The reaction is carried out at 200° to 275° C. with the evolution of water. Amines include lauryl amine, hexadecyl amine, octadecyl amine, rosin amine and fatty acid amines.

U.S. Pat. No. 3,347,926 to J. D. Zech teaches a catalytic process for aminating primary and secondary aliphatic alcohols. The catalyst comprises a chromium-promoted Raney nickel. The reaction is carried out at 150° to 275° C. with ammonia, primary amines or secondary amines of 1 to 6 carbon atoms.

U.S. Pat. No. 2,923,696 to K. E. Harwell et al., teaches resinous compositions formed by the reaction of an epoxy resin with a high-boiling amine product. The patent further teaches hydrogenation catalysts employing copper, nickel, cobalt and oxides thereof.

U.S. Pat. No. 4,130,590 to Hobbs et al., teaches the production of long-chain unsaturated amines such as N-(alkadienyl)amines and saturated or hydrated derivatives thereof.

U.S. Pat. No. 3,654,370 to E. Pechhold teaches a process for preparing a polyurethane which is the reaction product of (a) an oligomer formal diol made by coupling segments of copolymers of tetrahydrofuran and an alkylene oxide, such as propylene oxide, with formaldehyde, (b) an organic polyisocyanate and a chain extender as exemplified by ethylene glycol, glycerine, etc.

U.S. Pat. No. 4,691,000 to Andre Collart et al., teaches a process for preparing copolymers containing oxymethylene and 2-fluoromethoxyethylene repeating units formed by copolymerizing trioxane with a derivative of a cyclic ether, such as epifluorohydrin.

SUMMARY OF THE INVENTION

This invention relates to compounds of the formula:

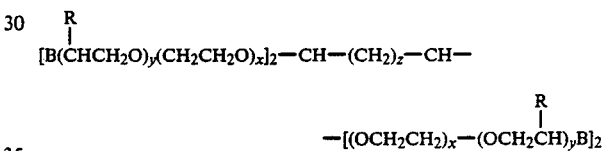

wherein
R is selected from the group consisting of the methyl or ethyl radical,
x ranges from 2 to about 50,
y ranges from 2 to about 24,
z is 0 to 3,
B is $-NH_2$ or $-OH$, and wherein at least one of the B substituents is $-NH_2$.

In addition to the products of this invention where the four B substituents are $-NH_2$ groups, this invention also relates to compounds wherein one, two or three of the B substituents are $-NH_2$ groups with the balance of the B substituents being $-OH$ groups. Preferably, the sum of x+y ranges from about 4 to 45 and R is the methyl radical.

The process for preparing the amine products of this invention comprises:

a) reacting a dialdehyde of the formula $OHC-(CH_2)_z-CHO$, wherein z is 0–3, with a polyoxyalkylene glycol having a molecular weight of up to about 2000 at a temperature of about 100° to about 150° C. and in the presence of a catalyst such as methane sulfonic acid, to form a dialdehyde glycol condensate having four hydroxylterminated oxyethylene groups;

b) alkoxylating the said condensate with propylene oxide, butylene oxide or mixtures thereof to form the corresponding glycol adduct; and c) catalytically aminating the said glycol adduct in the presence of hydrogen and ammonia to form the amine compound.

The sequence of reaction steps whereby the amine compounds of this invention are prepared is set out below where for purposes of illustration the dialdehyde employed is glyoxal:

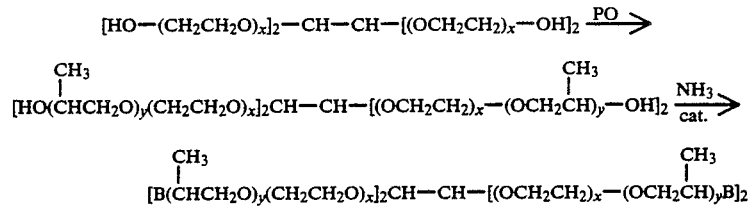

In the above reaction sequence x ranges from 2 to about 50, y ranges from 2 to about 24, B is $-NH_2$ or $-OH$ and at least one of the B substituents is $-NH_2$.

One very important improvement over the art is that the dialdehyde glycol condensates formed in step (a) of the process, which are used as initiator polyols, are liquid products which are easier to handle than solids.

The amine compounds of this invention are especially useful in preparing a variety of polyurea products such as RIM elastomers with high molecular weights which exhibit excellent flexibility. The composition of the amine products can be varied widely in that both large and small chains may be obtained to form a mixture of products with unique distributions since the substituents may be separately specified.

Reaction Injection Molding (RIM) is a technique for the rapid mixing and molding of large, fast-curing urethane parts. RIM polyurethane parts are used in a variety of exterior body applications on automobiles where the light weight contributes to energy conservation. RIM parts are generally made by rapidly mixing active hydrogen-containing materials with polyisocyanate and placing the mixture into a mold where reaction proceeds. After reaction and demolding, the parts may be subjected to an additional curing step which comprises placing the parts in an oven, held at 250° F. or higher.

It also has been found that the products of this invention are useful as curing agents in forming epoxy resin compositions, castings, etc.

DESCRIPTION OF THE PREFERRED EMBODIMENTS

A wide variety of catalysts are suitable for use in preparing the dialdehyde glycol condensates formed in step (a) of the above-described process. Catalysts which may be employed in step (a) include, for example, methane sulfonic acid, p-toluene sulfonic acid, sulfuric acid, AMBERLYST ® 15 ion-exchange resin made by the Rohm and Haas Company of Philadelphia, Pa., and NAFION ® NR-50, an ion-exchange resin made by DuPont.

The alkoxylation reaction of step (b) of the above-described process is carried out according to methods well known in the art and as set out in the Examples.

Amination of the alkoxylate formed in step (b) of the above-described process is conducted as set out in U.S. Pat. No. 3,654,370 to E. L. Yeakey, which describes the amination of polyoxyalkylene polyols to form the corresponding amines. The amination of step (c) of the above-described process is conducted in the presence of a hydrogenation-dehydrogenation catalyst prepared, for example, from a mixture of the oxides of nickel, copper and chromium and in the presence of ammonia and hydrogen at a temperature of about 150° to about 250° C., preferably about 190° to about 240° C. and at a pressure of about 1000 to about 4000 psig, preferably at about 1500 to about 2500 psig.

Other useful hydrogenation-dehydrogenation catalysts include Raney nickel, promoted Raney nickel such as molybdenum promoted Raney nickel; Ni/Cu/Cr powder; Ni/Cu/Cr/Mo/Al powder, etc.

The following examples which illustrate the nature of the instant invention are not intended to be limitative.

EXAMPLE 1

Preparation of a Tetraethylene Glycol/Glyoxal Condensate Using an Ion-Exchange Resin Catalyst Into a one-liter, four-necked flask equipped with a stirrer, thermometer, Dean-Stark trap, water condenser and nitrogen source were charged 400 g tetraethylene glycol, 75 g aqueous 40% glyoxal, and 10.8 g NAFION ® NR-50 ion-exchange resin made by DuPont. The reactants were then heated at 110°-125° C. for 3.5 hours during which time 43.8 g water were collected in the Dean-Stark trap. The product was then stripped under vacuum (5-10 mm) for 1.75 hours. The product was then separated from the ion-exchange resin by filtration. Analyses of the product were as follows:

| Run No. | 6276-75 |
|---|---|
| Properties | |
| Acid no., mg KOH/g | 0.39 |
| Hydroxyl no., mg KOH/g | 320 |
| Viscosity, °F., cs | |
| 77 | 477 |
| 100 | 220 |
| Appearance | Brown viscous liquid |

The $^{13}C$ NMR spectra of the product indicated that 75% of the tetraethylene glycol had reacted to form:

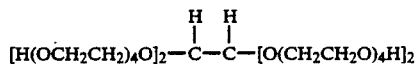

EXAMPLE 2

Preparation of a Tetraethylene Glycol/Glyoxal Condensate Using a Methane Sulfonic Acid Catalyst Using the apparatus described in Example 1, 400 g tetraethylene glycol, 75 g 40% aqueous glyoxal, 0.22 g methane sulfonic acid, and 75 g toluene were heated 6.6 hours at 120°-134° C. during which time 56.3 g water was collected in the Dean-Stark trap. The product was then vacuum stripped at 5 mm for 1.5 hours. Analyses of the finished product were as follows:

| Sample No. | 6276-81 |
|---|---|
| Properties | |
| Acid no., mg KOH/g | 0.425 |
| Hydroxyl no., mg KOH/g | 311 |
| Viscosity, °F., cs | |
| 77 | 2470 |
| 100 | 1142 |
| Appearance | Yellow viscous liquid |

The $^{13}$C NMR verified the structure shown in Example 1.

EXAMPLE 3

Scale-Up Preparation of the Product of Example 2

Using the procedure of Example 2, 1423 g tetraethylene glycol, 265.9 g aqueous 40% glyoxal, 0.66 g methane sulfonic acid, and 150 g toluene were heated 5.4 hours at 118°-168° C. The finished product was a light yellow viscous liquid which had the following properties:

| Sample No. | 6376-18 |
|---|---|
| Properties | |
| Acid no., mg KOH/g | 0.30 |
| Hydroxyl no., mg KOH/g | 297 |
| Water, wt. % | 0.065 |
| pH in 10:6 isopropanol-water | 4.2 |
| Viscosity, 77° F., cps | 3895 |

The $^{13}$C NMR spectra showed that 80% of the tetraethylene glycol had reacted to form the product described in Example 2.

EXAMPLE 4

Preparation of a Triethylene Glycol/Glyoxal Condensate Using Methane Sulfonic Acid Catalyst Using the procedure of Example 2, 408.3 g triethylene glycol, 98.6 g 40% aqueous glyoxal, 0.2 g methane sulfonic acid, and 200 ml toluene were reacted at 100°-125° C. for 4.5 hours during which time 79.1 g water was collected in the Dean-Stark trap. The finished product had the following properties:

| Run No. | 6367-35 |
|---|---|
| Properties | |
| Acid no., mg KOH/g | 0.075 |
| Hydroxyl no., mg KOH/g | 428 |
| Water, wt. % | 0.0244 |
| pH in 10:6 isopropanol-water | 5.3 |
| Viscosity, °F., cs | |
| 77 | 1157 |
| 100 | 523 |
| Appearance | Light yellow viscous liquid |

EXAMPLE 5

Preparation of a Polyether Tetrol Using the Tetraethylene Glycol/Glyoxal Condensate of Example 3 as the Initiator Into a one-half gallon stirred autoclave were charged 1000 g of the tetraethylene glycol/glyoxal condensate of Example 3 and 44.4 g 45% aqueous potassium hydroxide. The reactor was then purged with prepurified nitrogen. Maintaining a nitrogen purge, the reactor was heated to 100° C. and vacuum stripped to a minimum pressure at 100° C. Propylene oxide (190 g) was then reacted at 100°-111° C. at 50 psig. The reaction mixture was then digested to a minimum pressure. The alkaline product was neutralized by stirring with 178 g magnesium silicate for two hours at 95° C. after which the neutralized product was vacuum stripped to a minimum pressure, nitrogen stripped and filtered. The finished product had the following properties:

| Sample No. | 6364-67 |
|---|---|
| Properties | |
| Acid no., mg KOH/g | 0.034 |
| Hydroxyl no., mg KOH/g | 269 |
| Water, wt. % | 0.3 |
| pH in 10:6 isopropanol-water | 9.2 |
| Viscosity, 77° F., cs | 2220 |
| Appearance | Brown, viscous liquid |

EXAMPLE 6

Preparation of a Polyether Tetrol Using a Polyol Prepared as Described in Example 1 as the Initiator Into a one-half gallon stirred autoclave were charged 250 g of the initiator and 13.8 g 40% aqueous potassium hydroxide. The reactor was then purged with prepurified nitrogen. Maintaining a nitrogen purge, the reactor was heated to 100° C. and the initiator was dewatered by vacuum and nitrogen stripping. Propylene oxide (1087 g) was then reacted at 105°-110° C. at 50 psig over a 2.8 hour period. The alkaline product was neutralized by stirring two hours at 95° C. with 50 g magnesium silicate 30/40 which was added as an aqueous slurry following which di-t-butyl p-cresol (1.3 g) was added for stabilization of the product. The neutralized product was then vacuum stripped to a minimum pressure, nitrogen stripped and filtered. Properties of the product were as follows:

| Sample No. | 6364-91 |
|---|---|
| Properties | |
| Acid no., mg KOH/g | 0.016 |
| Hydroxyl no., mg KOH/g | 105 |
| Water, wt. % | 0.18 |
| pH in 10:6 isopropanol-water | 7.6 |
| Viscosity, °F., cs | |
| 77 | 648 |
| 100 | 322 |
| Appearance | Brown, viscous liquid |

EXAMPLE 7

Preparation of a Polyether Tetrol Using the Polyol Described in Example 4 as the Initiator Into a one-half gallon stirred autoclave were charged 150 g of the initiator polyol and 6.75 g 45% aqueous potassium hydroxide. The reactor was then purged with prepurified nitrogen. Maintaining a nitrogen purge, the reactor was heated to 100° C. and the initiator dried by vacuum and nitrogen stripping. Propylene oxide (995 g) was then reacted at 110°-115° C. at 50 psig over a 3.25 hour period. After digestion to an equilibrium pressure, the alkaline product was neutralized by stirring two hours at 95° C. with 27 g magnesium silicate 30/40 which was added as an aqueous slurry. Di-t-butyl=p-cresol (1.1 g) was then added to stabilize the product. The neutralized product was then vacuum stripped to a minimum pressure, nitrogen stripped, and filtered. The finished product had the following properties:

| Run No. | 6405-3 |
|---|---|
| Properties | |
| Acid no., mg KOH/g | 0.02 |
| Hydroxyl no., mg KOH/g | 78.5 |
| Viscosity, °F., cs | |
| 77 | 469 |
| 100 | 231 |
| Appearance | Brown, viscous liquid |

EXAMPLE 8

Reductive Amination of the Glyoxal-Tetraethylene Glycol-Propylene Oxide Adduct of Example 5 Using a Nickel Catalyst The tetrol (100 g) and powdered Ni/Cu/Cr catalyst (15 g) were charged into a 300 ml stirred autoclave which was then sealed and flushed with hydrogen. Ammonia (20 g) was then introduced into the autoclave from a sample bomb. 400 psig pressure of hydrogen was then pressured into the reactor above the autogenous pressure (~50 psig). The mixture was then heated to 230° C. with stirring for one hour. A maximum pressure of 1675 psig was recorded during the process. After cooling to room temperature, the product was filtered and volatiles, which included water, were removed by vacuum stripping. The product was a light brown liquid which had the following properties: total acetylatables, meq/g 4.82, total amines, meq/g 1.62, primary amine, meq/g 1.60. Basis these analyses, the product contained 32.6 percent primary amine groups.

EXAMPLE 9

Reductive Amination of the Glyoxal-Tetraethylene Glycol-Propylene Oxide Adduct of Example 6 Using a Ni/Cu/Cr/Mo/Al Catalyst.

The procedure of Example 8 was repeated using 100 g polyol, 15 g powdered Ni/Cu/Cr/Mo/Al catalyst, and 21 g ammonia. The operating conditions were 230° C. and 1650 psig for one hour. The resultant product was a light colored liquid which had the following properties: total acetylatables, meq/g 1.45, total amine, meq/g 0.98. Basis these analyses, the product contained 67.6 percent primary amine groups.

EXAMPLE 10

Reductive Amination of the Glyoxal-Tetraethylene Glycol-Propylene Oxide Adduct of Example 5 Using a Ni/Cu/Cr/Mo Catalyst Using the procedure of Example 8, polyol (100 g), powdered Ni/Cu/Cr/Mo/Al catalyst (15 g) and ammonia (21 g) were reacted for one hour at 230° C. and 1525 psig pressure. The finished product was a light brown liquid which had the following properties: total acetylatables, meq/g 4.63, total amine meq/g 1.95. Basis these analyses, the product contained 42.1 percent primary amine groups.

EXAMPLE 11

Reductive Amination of the Glyoxal-Tetraethylene Glycol-Propylene Oxide Polyol of Example 6 Using a Ni/Cu/Cr/Mo/Al Catalyst Using the procedure of Example 8, polyol (100 g), powdered Ni/Cu/Cr/Mo/Al catalyst (15 g), and ammonia (21 g) were reacted for one hour at 230° C. and 1600–1650 psig pressure. The resultant hydroxyl amine was a yellow-brown liquid which had the following properties: total acetylatables, meq/g, 1.52, total amine, meq/g 0.556. Basis these analyses, the product contained 36.6 percent primary amine groups.

EXAMPLE 12

Reductive Amination of the Glyoxal-Tetraethylene Glycol-Propylene Oxide Adduct of Example 6 Using a Ni/Cu/Cr/Mo/Al Catalyst Using the conditions of Example 9, the polyol was converted into a hydroxyl amine using the following reaction conditions: 225° C., four hours. The resultant product had the following properties: total amine, meq/g, 1.37; total amine, meq/g 0.562. The $^{13}C$ NMR spectra showed that the product contained 35% —$CH(CH_3)$—$NH_2$ and 65% —$CH(CH_3)$—OH.

EXAMPLE 13

Reductive Amination of the Glyoxal-Tetraethylene Glycol-Propylene Oxide Adduct of Example 6 Using Raney Nickel Catalyst The procedure of Example 8 was repeated using 30 g Raney nickel catalyst.

The polyol from Example 6 (150 g), ammonia (36 g) and catalyst were heated for three hours at 230° C. at 3600 psig. The resultant product had the following properties: total acetylatables, meq/g 1.40, total amine, meq/g 0.90. Basis these analyses, the product contained 64.3 percent primary amine groups.

EXAMPLE 14

Reductive Amination of the Glyoxal-Triethylene Glycol-Propylene Oxide Adduct of Example 7 Using Raney Nickel Catalyst The procedure of Example 8 was repeated using powdered Raney nickel catalyst (30 g). The polyol of Example 7 (150 g), ammonia (30 g), and catalyst were heated at 230° C. for four hours at a pressure of 3000 psig. The product was a light yellow liquid which analyzed as follows: total acetylatables, meq/g 1.25, total amine, meq/g 0.767, primary amine, meq/g 0.754, color Pt-Co 150. Basis these analyses, the product contained 60.3 percent primary amine groups.

EPOXY RESIN COMPOSITIONS

This invention also relates to epoxy resin compositions, such as films, castings, adhesives, etc., comprising a vicinal polyepoxide having an epoxide equivalency greater than about 1.8 and a curing amount of a curing agent comprising an amine compound of this invention and a polyoxyalkylenepolyamine for example, including, but not limited to, polyoxyalkylenediamines of the D-series as exemplified by:

JEFFAMINE ®D-230 having the formula:

-continued

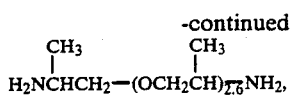

JEFFAMINE ®D-400 having the formula:

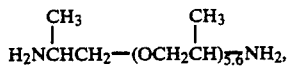

JEFFAMINE ®D-2000 having the formula:

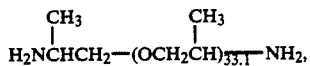

polyoxyalkylenediamines of the EDR-series as exemplified by JEFFAMINE ® EDR-148 having the formula:

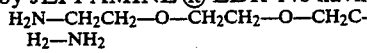

and polyoxyalkylenetriamines, such as the JEFFAMINE ® T-series, as exemplified by JEFFAMINE ® T-403 having the formula:

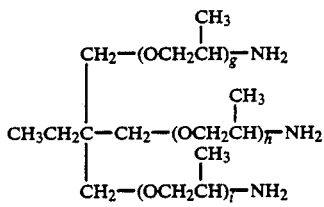

wherein the sum of g+h+i is about 5.3, and JEFFAMINE ® T-5000 having the formula:

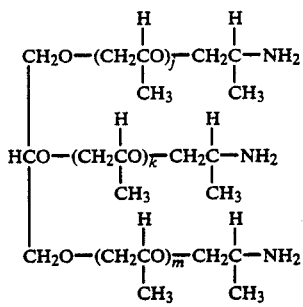

wherein the sum of j+k+m is about 85. All of the above JEFFAMINE ® products are marketed by the Texaco Chemical Company, Houston, Tex.

Usually the curing agent will comprise from about 15 to about 60 weight percent of the amine compound of this invention with the balance being the polyoxyalkylenepolyamine.

Generally, the amine-cured vicinal polyepoxide-containing compositions are organic materials having an average of at least 1.8 reactive 1,2-epoxy groups per molecule. These polyepoxide materials can be monomeric or polymeric, saturated or unsaturated, aliphatic, cycloaliphatic, aromatic or heterocyclic, and may be substituted if desired with other substituents besides the epoxy groups; e.g., hydroxyl groups, ether radicals, aromatic halogen atoms and the like.

Preferred polyepoxides are those of glycidyl ethers prepared by epoxidizing the corresponding allyl ethers or reacting, by known procedures, a molar excess of epichlorohydrin and an aromatic polyhydroxy compound; i.e., isopropylidene bisphenol, novolak, resorcinol, etc. The epoxy derivatives of methylene or isopropylidene bisphenols are especially preferred.

A widely-used class of polyepoxides which are useful according to the instant invention includes the resinous epoxy polyethers obtained by reacting an epihalohydrin, such as epichlorohydrin, etc., with either a polyhydric phenol or a polyhydric alcohol. An illustrative, but by no means exhaustive, listing of suitable dihydric phenols includes 4,4'-isopropylidene bisphenol, 2,4'-dihydroxydiphenylethylmethane, 3,3'-dihydroxydiphenyldiethylmethane, 3,4'-dihydroxydiphenylmethylpropylmethane, etc.

Among the polyhydric alcohols which can be co-reacted with an epihalohydrin to provide these resinous epoxy polyethers are such compounds as ethylene glycol, propylene glycols, butylene glycols, pentane diols, bis(4-hydroxycyclohexyl)dimethylmethane, 1,4-dimethylolbenzene, glycerol, 1,2,6-hexanetriol, trimethylolpropane, mannitol, sorbitol, erythritol, pentaerythritol, their dimers, trimers and higher polymers, e.g., polyethylene glycols, polypropylene glycols, triglycerol, dipentaerythritol and the like, polyallyl alcohol, polyhdric thioethers, etc.

Another class of polymeric polyepoxides which can be amine-cured in accordance with the instant invention includes the epoxy novolak resins obtained by reacting, preferably in the presence of a basic catalyst; e.g., sodium or potassium hydroxide, an epihalohydrin, such as epichlorohydrin, with the resinous condensate of an aldehyde; e.g., formaldehyde, and either a monohydric phenol; e.g., phenol itself, or a polyhydric phenol.

Optionally, the epoxy resin formulations of the instant invention can include an "accelerator" to speed the amine cure of the epoxy resin, especially at ambient temperatures. In several applications, such acceleration is beneficial, especially when an epoxy resin is used as an adhesive in flammable environment, thus making elevated temperature cure inconvenient or even hazardous. Lee, H. and Neville, K., HANDBOOK OF EPOXY RESINS, pp. 7–14, describes the use of certain amine-containing compounds as epoxy curing agent-accelerators.

Many accelerators are known in the art which can be utilized in accordance with the instant invention. Examples include salts of phenols, salicyclic acids, amine salts of fatty acids, such as those disclosed in U.S. Pat. No. 2,681,901, and tertiary amines such as those disclosed in U.S. Pat. No. 2,839,480.

It will further be realized that various conveniently employed additives can be admixed with the polyepoxide-containing composition of the instant invention prior to final cure. For example, in certain instances it may be desired to add minor amounts of hardeners along with various other accelerators and curing agent systems well known in the art. Additionally, conventional pigments, dyes, fillers, flame-retarding agents can be added.

EXAMPLE 15

Curing of an Epoxy Resin with the Aminated Glyoxal-Triethylene Glycol-Propylene Oxide Adduct of Example 14

Epon ® 828, a diglycidyl ether of Bisphenol A made by the Shell Chemical Co. (10 g), JEFFAMINE ® EDR-148, triethylene glycol diamine made by the Texaco Chemical Co. (1.8 g), and the aminated glyoxal-triethylene glycol-propylene oxide adduct of Example 14 (3.6 g) were thoroughly mixed with a metal spatula and allowed to stand at room temperature for approximately six hours. The material cured into a hard, opaque resin during that period. The above mixture could also be cured within 30 minutes at 80° C. to form a hard, opaque, epoxy resin.

PREPARATION OF POLYUREA ELASTOMERS

As previously pointed out, the amine compounds of this invention are useful in preparing polyurea elastomers by reaction with a polyisocyanate. Optional additives include chain extenders, catalysts, filler materials, etc. Preferably, the tetra-functional amino alcohol will have a molecular weight of about 500 to about 6000.

A wide variety of aromatic and aliphatic polyisocyanates can be utilized in making the polyurea elastomers of this invention.

Typical aromatic polyisocyanates include p-phenylene diisocyanate, polymethylene polyphenylisocyanate, 2,6-toluene diisocyanate, dianisidine diisocyanate, bitolylene diisocyanate, naphthalene-1,4-diisocyanate, bis(4-isocyanatophenyl)methane, bis(3-methyl-3-isocyanatophenyl)methane, bis(3-methyl-4-isocyanatophenyl)methane, and 4,4'-diphenylpropane diisocyanate.

Other aromatic polyisocyanates used in the practice of the invention are methylene-bridged polyphenyl polyisocyanate mixtures which have a functionality of from about 2 to about 4. These isocyanate compounds are produced by the phosgenation of corresponding methylene bridged polyphenyl polyamines, which are conventionally produced by the reaction of formaldehyde and primary aromatic amines, such as aniline, in the presence of hydrochloric acid and/or other acidic catalysts. Known processes for preparing polyamines and corresponding methylene-bridged polyphenyl polyisocyanates therefrom are described in U.S. Pat. Nos. 2,683,730; 2,950,263; 3,012,008; 3,344,162 and 3,362,979.

Usually methylene-bridged polyphenyl polyisocyanate mixtures contain about 20 to about 100 wt % methylene diphenyldiisocyanate isomers, with the remainder being polymethylene polyphenyl diisocyanates having higher functionalities and higher molecular weights. Typical of these are polyphenyl polyisocyanate mixtures containing about 20 to 100 wt % methylene diphenyldiisocyanate isomers, of which 20 to about 95 wt % thereof is the 4,4'-isomer with the remainder being polymethylene polyphenyl polyisocyanates of higher molecular weight and functionality that have an average functionality of from about 2.1 to about 3.5. These isocyanate mixtures are commercially available and can be prepared by the process described in U.S. Pat. No. 3,362,979 to Floyd E. Bentley.

The most preferred aromatic polyisocyanate is methylene bis(4-phenylisocyanate) or MDI. Pure MDI, quasiprepolymers of MDI and modified pure MDI are all useful in the preparation of RIM elastomers. Since pure MDI is a solid and, thus, often inconvenient to use, liquid products based on MDI are often used and are included in the scope of the terms MDI or methylene bis(4-phenylisocyanate) used herein. U.S. Pat. No. 3,394,164 is an example of a liquid MDI product. More generally, uretonimine modified pure MDI is included also. This product is made by heating pure distilled MDI in the presence of a catalyst to give a mixture of pure MDI and modified MDI. Preferably the amount of isocyanates used is the stoichiometric amount based on all the ingredients in the formulation or greater than the stoichiometric amount. Examples of commercial materials of this type are Upjohn's Isonate ® 125M (pure MDI) and Isonate ® 143L (liquid MDI).

Chain extenders useful in preparing the elastomers of this invention are preferably difunctional. Mixtures of difunctional and trifunctional chain-extenders are also useful in this invention. The chain-extenders useful in this invention include diols, amino alcohols, diamines or mixtures thereof. Low molecular weight linear diols such as 1,4-butanediol and ethylene glycol have been found suitable for use in this invention. Ethylene glycol is especially preferred. These chain-extenders produce a polymer having a high glass transition temperature and/or high melting points when reacted with a suitable diisocyanate. It has been discovered that the polyurethane polymers of this invention which have a high glass transition temperature and a high melting point also show the improved properties in the process of this invention. Other chain-extenders including cyclic diols such as 1,4-cyclohexane diol and ring containing diols such as bis(hydroxyethyl)hydroquinone, amide or ester containing diols or amino alcohols, aromatic diamines and aliphatic amines are also suitable as chain-extenders in the practice of this invention.

Although not essential, additives which enhance the color or properties of the polyurea elastomer may be used. For example, chopped or milled glass fibers, chopped or milled carbon fibers and/or other mineral fibers are useful.

The preparation of the polyurea elastomers of this invention is described in the following example which is not to be construed as limiting in any way.

EXAMPLE 16

Preparation of a Polyurea Elastomer by Reaction of a Diisocyanate and the Aminated Glyoxal-Tetraethylene GlycolPropylene Oxide Adduct of Example 10

This example illustrates the reactivity of the aminated glyoxal-tetraethylene glycol-propylene oxide polyol of Example 10 with diphenyl methane diisocyanate (ISONATE ® 143L, The Upjohn Co.). The aminated polyol (8.76 g) and ISONATE ® 143L (1.24 g) were rapidly mixed with a metal spatula. The reactants reacted quite rapidly to form an elastomer.

What is claimed is:

1. A compound of the formula:

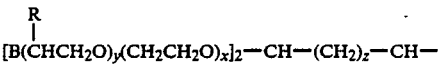

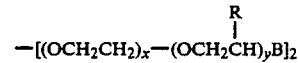

wherein
R is selected from the group consisting of the methyl or ethyl radical,
x ranges from 2 to about 50,
y ranges from 2 to almost 24,
z is 0 to 3, and
B is —NH$_2$ or —OH, and wherein at least one of the B substituents is —NH$_2$.

2. The compound of claim 1 wherein B is —NH$_2$.

3. The compound of claim 1 wherein R is the methyl radical.

4. The compound of claim 1 wherein R is the ethyl radical.
5. The compound of claim 1 wherein x is 3.
6. The compound of claim 1 wherein x is 4.
7. The compound of claim 1 wherein z is 0.
8. The compound of claim 1 wherein z is 1.
9. The compound of claim 1 wherein x is 3 and z is 0.
10. The compound of claim 1 wherein x is 4, and z is 0.

* * * * *